United States Patent [19]

Bruynes et al.

[11] 4,182,870

[45] Jan. 8, 1980

[54] PREPARATION OF 3-BROMOMETHYL-3-CEPHEM SULFOXIDES

[75] Inventors: Cornelis A. Bruynes, Koudekerk; Jan J. de Koning, Rijswijk, both of Netherlands

[73] Assignee: Gist-Brocades N.V., Delft, Netherlands

[21] Appl. No.: 937,989

[22] Filed: Aug. 30, 1978

[30] Foreign Application Priority Data

Sep. 7, 1977 [GB] United Kingdom ............... 37413/77

[51] Int. Cl.² .......................................... C07D 501/04
[52] U.S. Cl. ...................................... 544/16; 424/246
[58] Field of Search .......................................... 544/16

[56] References Cited
U.S. PATENT DOCUMENTS 4,042,585  8/1977  Koppel .................................... 544/16

*Primary Examiner*—Nicholas S. Rizzo

*Attorney, Agent, or Firm*—Hammond & Littell, Weissenberger and Muserlian

[57] ABSTRACT

An improved process for the preparation of 3-bromomethyl-3-cephem sulfoxide derivatives of the formula

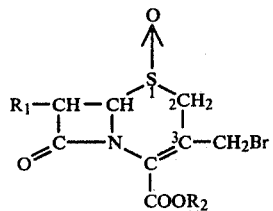

wherein $R_1$ is an acylamido group and $R_2$ is a group protecting the carboxy radical which are valuable intermediates for the preparation of various therapeutically useful cephalosporanic acid derivatives.

15 Claims, No Drawings

PREPARATION OF 3-BROMOMETHYL-3-CEPHEM SULFOXIDES

STATE OF THE ART

British Pat. No. 1,326,531 describes an elaborate bromination step to form the compounds of formula I which can then be readily reacted to replace the bromine atom by various nucleophilic atoms or groups to give 3'-nucleophilic substituted desacetoxy-cephalosporanic acid derivatives which are, or can be converted by methods known per se into, antibiotically active cephalosporanic derivatives. The said bromination process is effected in manner known per se of corresponding desacetoxy-3-cephem sulfoxides of the formula

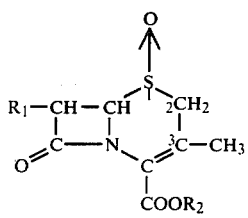

wherein $R_1$ and $R_2$ are hereinbefore defined, and separation is made of the desired 3-bromomethyl-3-cephem sulfoxides of formula I from the reaction mixture. This straightforward procedure does not give very satisfactory yields of the desired products, inter alia because side-reactions can take place whereby bromine is introduced into other positions than that of the 3-methyl group of the compounds of formula II, for example in the 2-position.

OBJECTS OF THE INVENTION

It is an object of the invention to provide an improved process for the preparation of the 3-bromomethyl compounds of formula I.

It is another object of the invention to provide novel intermediates produced in the process.

These and other objects and advantages of the invention will become obvious from the following detailed description.

THE INVENTION

The improved process of the invention for the preparation of compounds of the formula

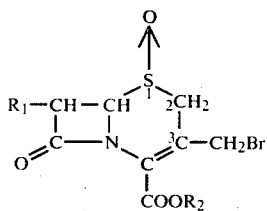

wherein $R_1$ is an acylamido group and $R_2$ is a group protecting the carboxy radical comprises brominating a compound of the formula

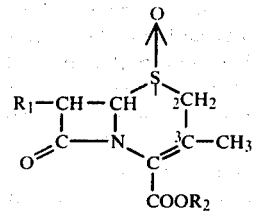

wherein $R_1$ and $R_2$ have the above definition to obtain a mixture of compounds of the formulae

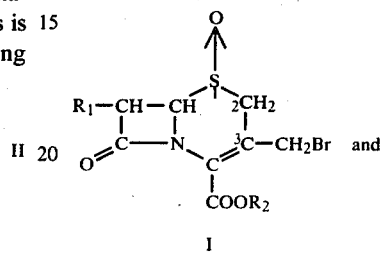

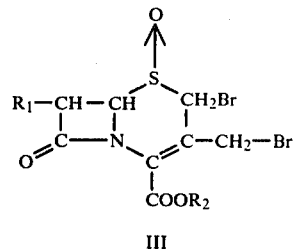

and treating the mixture or the compound of formula III with a debrominating agent in the presence of a hydrogen donor to selectively remove the 2-bromine. The desired product of formula I may then be recovered by conventional means.

The acylamido of $R_1$ can be any group—hitherto disclosed in the chemical literature including patent specifications or known to those skilled in the art of penicillin or cephalosporin chemistry—attached to the 6-position in natural or synthetic penicillin compounds or attached to the 7-position of natural or synthetic cephalosporin compounds. Preferably, the acylamido group is one present in the 6β-side chain of penicillins that can be obtained by fermentative procedures which penicillins can readily be converted into cephem sulfoxides by known methods. Suitable groups of $R_1$ are for example, phenylacetamido, phenoxyacetamido, benzamido and formamido.

$R_2$ can be any group known to those skilled in the art for protecting the carboxy radical of penicillanic acid or cephalosporanic acid derivatives, but preferably $R_2$ is an ester group which can be readily introduced and easily removed again after the reaction has been completed. Suitable ester groups are, for example, straight- or branched-chain alkyls of 1 to 4 carbon atoms optionally substituted by one or more halogen atoms or by one or two phenyl groups, which phenyl groups may themselves carry one or more substituents such as nitro and methoxy groups, and silyl groups, for example trialkylsilyl groups. Particularly suitable ester groups are the methyl, t-butyl, 2-bromoethyl, 2,2,2-trichloroethyl, benzyl, 4-nitrobenzyl, 4-methoxybenzyl, benzhydryl and trimethylsilyl groups.

The yields of the process are considerably higher than the prior art processes as the undesired by-product of formula III is converted into the desired compound of formula I. Another undesired side-reaction product which can be present in the reaction mixture obtained after bromination of the compounds of formula II is the corresponding 2-bromo-3-methyl-3-cephem sulfoxide. When this product is present in said reaction mixture, it will be converted back again to the starting material of formula II during the debromination reaction described above.

This conversion is an additional advantage of the process of the invention since it prevents loss of starting material in the form of the undesired 2-bromo-3-methyl derivative which is recycled as the starting material and this can then be used again in the improved bromination process of the invention. By the process of the present invention, the yields of the 3-bromomethyl-3-cephem sulfoxide derivatives of formula I obtained can be improved considerably as compared with the known processes for the bromination of desacetoxy-3-cephem sulfoxides of the formula II.

Bromination of a desacetoxy-3-cephem sulfoxide of formula II to convert the methyl group in the 3-position to a bromomethyl group can be effected with known brominating agents such as N-bromoimides or N-bromoamides. Suitable brominating agents are, for example, 1,3-dibromo-5,5-dimethylhydantoin and N-bromosuccinimide.

The necessary activation of the brominating agent can be achieved by adding a free radical initiator to the reaction mixture or by irradiation of the reaction mixture with ultraviolet or visible light, e.g. electric light from a 150–500 W. lamp. Suitable free radical initiators are, for example, azo compounds such as azo-isobutyronitrile, and peroxides such as benzoyl peroxides. The reaction is preferably carried out in a suitable inert organic solvent, for example, methylene chloride or 1,2-dichloroethane.

When a free radical initiator is used for the activation of the brominating agent, the reaction is advantageously carried out at a temperature between 40° and 90° C. In the case where the activation is effected by irradiation of the reaction mixture with light, the temperature of the reaction mixture is preferably between −20° and 30° C.

There is usually obtained a mixture of bromination products consisting of the 2-bromo-3-methyl-, the 2-bromo-3-bromomethyl and the 3-bromomethyl derivatives of the starting 3-cephem sulfoxides of formula II. The quantities of the various bromination products thus obtained can be established by means of High Performance Liquid Chromatography (HPLC) analysis and depend on the nature of the starting sulfoxide of formula II, the brominating agent and bromination technique actually used and, generally, on the other reaction conditions employed during the bromination process. The various bromination products can be isolated from the reaction mixture in a manner known per se, for example, the reaction mixture may be evaporated to dryness and the products may be separated by chromatography of the residue on silica gel.

As aforementioned, the quantities of the various products in the reaction mixture can be established by HPLC analysis. In this method, the bromination products are first isolated in the manner described hereinbefore. Then, the content of the products and that of the starting material is determined by quantitative NMR analysis. These compounds are then used as references in the HPLC analysis to determine the quantities of the various products in the reaction mixture, before and after the debromination has been carried out. Before this analysis method is effected, the reaction mixtures have to be diluted to obtain concentrations suitable for this method. The values given in the Examples hereafter are always in relation to such diluted mixtures. This method of analysis has an accuracy of approximately 10%.

After the bromination of the desacetoxy-3-cephem sulfoxides of formula II, the reaction mixture containing 2-bromo-3-methyl-, 2-bromo-3-bromomethyl- and 3-bromomethyl-3-cephem sulfoxides is treated with a debrominating agent in the presence of a hydrogen donor to convert the 2-bromo-3-bromomethyl compound of formula III present therein to the desired 3-bromomethyl compound of formula I, and concurrently also a 2-bromo-3-methyl-3-cephem sulfoxide back again to a starting material of formula II which can then be used again.

Accordingly, after the bromination and debromination processes have been carried out, there is usually obtained a mixture mainly consisting of a 3-bromomethyl-3-cephem sulfoxide of formula I in admixture with some of the corresponding original starting material of formula II. The 3-bromomethyl-3-cephem sulfoxide of formula I thus obtained can be isolated from the reaction mixture in a manner known per se, for example, as described above for the mixture of bromination products.

Alternatively, a 2-bromo-3-bromomethyl-3-cephem sulfoxide of formula III present in the reaction mixture can, after separation and optional purification, by itself be treated with a debrominating agent in the presence of a hydrogen donor to convert it to a 3-bromomethyl compound of formula I.

The debromination is preferably carried out in a suitable organic solvent, for example, acetone, acetonitrile, acetic acid, dioxane, ethyl acetate, methylene chloride, 1,2-dichloroethane, 1,2-dimethoxyethane, tetrahydrofuran, 2-methoxyethanol, propylene carbonate, N,N-dimethylacetamide, bis(2-methoxyethyl)ether or tetrahydrothiopene 1,1-dioxide. Debromination of a 2-bromo-3-bromomethyl-3-cephem sulfoxide of formula III, as such or as present in the reaction mixture in which it is formed by the bromination of a compound of formula II, —to a 3-bromomethyl-3-cephem sulfoxide of formula I can be effected by treatment in the presence of a hydrogen donor with a trivalent organic phosphorus compound or an inorganic salt as the debrominating agent.

Suitable debrominating agents are selected from the group consisting of
(a) phosphites of the formula:

IV wherein $R_3$, $R_4$ and $R_5$ are individually selected from the group consisting of a straight- or branched-chain alkyl which may be substituted by a chlorine atom and has 1 to 18 carbon atoms, a phenyl group which may be substituted by a methyl group or a chlorine atom, an allyl and benzyl;

(b) other phosphites, for example phenyl neopentylglycol phosphite, poly(dipropyleneglycol)phenyl phosphite, tris 25 phosphite and tris(dipropyleneglycol)-phosphite;

(c) di- and triphosphites, for example diisodecyl pentaerythritol diphosphite, tetraphenyl dipropyleneglycol diphosphite, distearyl pentaerythritol diphosphite, diphenyl didecyl (2,2,4-trimethyl-1,3-pentanediol)diphosphite, tetrakis(nonylphenyl)polypropyleneglycol diphosphite and heptakis(dipropyleneglycol)triphosphite;

(d) phosphonites, for example di(lower alkyl)phenylphosphonites;

(e) phosphinites, for example lower alkyl diphenylphosphinites;

(f) phosphines, for example chlorodiphenylphosphine;

(g) other trivalent phosphorus compounds for example hexamethylphosphorous triamide, 2-ethoxy-4-methyl-1,3,2-dioxaphospholane, 4-methyl-2-piperidino-1,3,2-dioxaphospholane, diethyl N-methyl-N-phenylphosphoramidite and bis-o-phenylene pyrophosphite and (h) inorganic salts, for example stannous chloride ($SnCl_2$), sodium sulfite ($Na_2SO_3$) and sodium dithionite ($Na_2S_2O_4$).

The term "lower alkyl" as employed herein is meant to be straight- or branched-chain alkyls of 1 to 4 carbon atoms such as methyl, ethyl, allyl and t-butyl.

The debromination step is preferably carried out with at least an equimolar quantity of the debrominating agent in relation to the 2-bromo-3-bromomethyl compound of formula III and at ambient or somewhat lower temperatures. When the debrominating agent is of group (h) mentioned above, the ratio between the reactants should be approximately equimolar and when the debromination agent is of groups (a) to (g), a rather substantial excess of debrominating agent can be used as well.

Suitable debrominating agents of formula IV which may be used in the process of the invention are, for example, trimethyl phosphite, triethyl phosphite, tripropyl phosphite, triisopropyl phosphite, tributyl phosphite, triisobutyl phosphite, triamyl phosphite, trioctyl phosphite, triisooctyl phosphite, tris(2-ethylhexyl)-phosphite, tridecyl phosphite, triisodecyl phosphite, trineodecyl phosphite, trilauryl phosphite, tristearyl phosphite, triallyl phosphite, tris(2-chloroethyl)phosphite, triphenyl phosphite, tris(p-methylphenyl)phosphite, tris-O-tolyl phosphite, tris(p-chlorophenyl)phosphite, 2-ethylhexyl dioctyl phosphite, diethyl benzyl phosphite, didecyl phenyl phosphite, diisodecyl phenyl phosphite, isooctyl diphenyl phosphite, 2-ethylhexyl diphenyl phosphite, decyl diphenyl phosphite and isodecyl diphenyl phosphite.

Suitable phosphonites which may be used in the process of the invention are, for example, dimethyl phenylphosphonite, diethyl phenylphosphonite and di(t-butyl)phenylphosphonite. Suitable phosphinites are, for example, methyl diphenylphosphinite and ethyl diphenylphosphinite.

Particularly suitable are the following debrominating agents; trimethyl phosphite, triethyl phosphite, tributyl phosphite, triisooctyl phosphite, triisodecyl phosphite, trilauryl phosphite, tristearyl phosphite, triallyl phosphite, tris(2-chloroethyl)phosphite, triphenyl phosphite, tris-o-tolyl phosphite, tris(p-chlorophenyl)phosphite, 2-ethylhexyl dioctyl phosphite, diethyl benzyl phosphite, isooctyl diphenyl phosphite, 2-ethylhexyl diphenyl phosphite, isodecyl diphenyl phosphite, phenyl neopentylglycol phosphite, poly(dipropyleneglycol)-phenyl phosphite, tris 25 phosphite, tris(dipropyleneglycol)phosphite, diisocedyl pentaerythritol diphosphite, tetraphenyl dipropyleneglycol diphosphite, distearyl pentaerythritol diphosphite, diphenyl didecyl (2,2,4-trimethyl-1,3-pentanediol)diphosphite, tetrakis(nonylphenyl)polypropyleneglycol diphosphite, heptakis(dipropyleneglycol)triphosphite, bis-o-phenylene pyrophosphite, hexamethylphosphorous triamide, 2-ethoxy-4-methyl-1,3,2-dioxaphospholane, 4-methyl-2-piperidino-1,3,2-dioxaphospholane, diethyl N-methyl-N-phenylphosphoramidite, diethyl phenylphosphonite, methyl diphenylphosphinite and chlorodiphenylphosphine.

The debromination of inter alia the 2-bromo-3-bromomethyl-3-cephem sulfoxides of formula III should be carried out in the presence of a hydrogen donor which donor is usually already present in the reaction medium, for example in the form of water, etc. But in some cases it may be advantageous to add a hydrogen donor such as water, a lower alkanol such as methanol, or a carboxylic acid such as acetic acid to the reaction medium.

Some of the 3-cephem sulfoxides of formula III are new compounds such as the compounds conforming to that formula obtained as intermediate products in Example I(c), VI(d) and VIII(d), namely t-butyl 7-benzamido-2-bromo-3-bromomethyl-3-cephem-4-carboxylate 1-oxide, 2,2,2-trichloroethyl 7-formamido-2-bromo-3-bromomethyl-3-cephem-4-carboxylate 1-oxide and methyl 2-bromo-3-bromomethyl-7-phenylacetamido-3-cephem-4-carboxylate 1-oxide.

The starting materials of formula II which are brominated are known products or can be prepared by methods known per se. By the term "methods known per se" as used in this specification is meant methods heretofore used or described in the chemical literature.

In the following examples there are described several preferred embodiments to illustrate the invention. However, it is to be understood that the invention is not intended to be limited to the specific embodiments. The IR Spectra were taken as dispersion in KBr. To distinguish the various types of compounds in the reaction mixtures, the following notation is used throughout the Examples:

I: starting material
II: corresponding 3-bromomethyl derivative
III: corresponding 2-bromo derivative
IV: corresponding 2-bromo-3-bromomethyl derivative

EXAMPLE 1

STEP A:

A mixture of 103.2 g of dicyclohexylcarbodiimide, 43.5 g of t-butyl alcohol and 1.1 g of cuprous chloride was held at room temperature for 3 days and the mixture was then dissolved in 200 ml of methylene chloride. The resulting solution was added dropwise to a suspension of 35 g of 7-benzamido-3-methyl-3-cephem-4-carboxylic acid-1-oxide in 500 ml of methylene chloride and after stirring for 24 hours at room temperature, the precipitated N,N'-dicyclohexyl urea was removed by filtration and the precipitate washed with methylene chloride. The combined filtrates were washed sequentially with 2 N hydrochloric acid, saturated sodium bicarbonate solution (three times) and with water (twice). Methylene chloride was removed by evaporation in vacuo and toluene was added to the residue. The crystalline solid was isolated by filtration and washed with toluene. Upon crystallization from a methylene chloride/toluene mixture, 19.6 g (48% yield) of t-butyl 7-benzamido-3-methyl-3-cephem-4-carboxylate 1-oxide were obtained.

NMR Spectrum (CDCl$_3$): 1.56 (s, 9H), 2.14 (s, 3H), 3.11, 3.41, 3.52, 3.83 (ABq, 2H, J 18.5 Hz), 4.65 (br., 1H), 6.25 (dd, 1H, J 4.5 and 9.5 Hz), 7.37–7.97 (m, 5H), 7.56 (d, 1H, J 9.5 Hz)

IR Spectrum: 3400, 1770, 1715, 1685, 1520, 1030 cm$^{-1}$

STEP B:

4.2 ml (30 mmoles) of triethylamine and 3.28 g (24 mmoles) of N-bromosuccinimide were sequentially added to a solution of 7.8 g (20 mmoles) of t-butyl 7-benzamido-3-methyl-3-cephem-4-carboxylate 1-oxide in 150 ml of methylene chloride under nitrogen and cooled in an ice bath and the mixture was irradiated with a 150 W tungsten lamp for 15 minutes. The dark-brown reaction mixture was washed with a dilute hydrochloric acid solution (pH 1) and then twice with 250 ml portions of water. The organic layer was dried over magnesium sulfate, filtered and evaporated to dryness to obtain 10.6 g (70% yield-purity 62%) of t-butyl 7-benzamido-2-bromo-3-methyl-3-cephem-4-carboxylate 1-oxide.

NMR Spectrum (CDCl$_3$): 1.56 (s, 9H), 2.21 (s, 3H), 5.21 (s, 1H), 5.25 (d, 1H, J 4.8 Hz), 6.33 (dd, 1H, J 4.8 and 10 Hz), 7.3–7.96 (m, 5H), 7.41 (d, 1H, J 10 Hz).

IR Spectrum: 3400, 1800, 1730, 1675, 1520, 1055 cm$^{-1}$.

STEP C:

11.7 g (30 mmoles) of t-butyl 7-benzamido-3-methyl-3-cephem-4-carboxylate 1-oxide were dissolved in 250 ml of methylene chloride and the solution was kept under nitrogen and cooled in ice while 5.3 ml (45 mmoles) of triethylamine and 6.4 g (36 mmoles) of N-bromosuccinimide were subsequently added. The resulting solution was irradiated with a 150 W tungsten lamp for 20 minutes and the dark-brown solution was washed with dilute hydrochloric acid (pH 1) and with water. After drying over magnesium sulfate, the solution was concentrated by evaporation to approximately 100 ml. To the solution of t-butyl 7-benzamido-2-bromo-3-methyl-3-cephem-4-carboxylate 1-oxide thus obtained were added 100 ml of acetic acid and the resulting solution was held under nitrogen and was cooled in ice and irradiated with a 150 W tungsten lamp. 7.15 g (40 mmoles) of N-bromosuccinimide were added thereto followed after 4 hours by another 1.78 g (10 mmoles) of the same compound. Then, the solution was irradiated with a 150 W tungsten lamp for another 3 hours. Part of the solution thus obtained (52%), which contained t-butyl 7-benzamido-2-bromo-3-bromomethyl-3-cephem-4-carboxylate 1-oxide, was washed 4 times with 100 ml of water. After drying over magnesium sulfate, the solution was concentrated by evaporation to approximately 25 ml. Then, 5 ml of methanol were added thereto and the solution was treated with activated charcoal. After addition of 1,2-dichloroethane, the solution was evaporated to dryness and the residue was dissolved in diethyl ether. The product was precipitated with n-heptane to obtain 6.8 g (79.4%) of t-butyl 7-benzamido-2-bromo-3-bromomethyl-3-cephem-4-carboxylate 1-oxide.

NMR Spectrum (CDCl$_3$+DMSO-D$_6$): 1.59 (s, 9H), 4.17, 4.34, 4.58, 4.75 (ABq, 2H, J 10.5 Hz), 5.34 (d, 1H, J 5 Hz), 5.73 (s, 2H), 6.35 (dd, 1H, J 5 and 9.5 Hz), approximately 7.34–7.98 (m, 5H), 7.71 (d, 1H, J 9.5 Hz).

IR Spectrum: 3380, 1790, 1725, 1680, 1520, 1050 cm$^{-1}$.

STEP D:

The remainder of the solution of the 2-bromo-3-bromomethyl compound obtained was used as such in the following debromination process. To this solution which contained at most 14.4 mmoles of t-butyl 7-benzamido-2-bromo-3-bromomethyl-3-cephem-4-carboxylate 1-oxide, were added 14 ml (approximately 25 mmoles) of triisodecyl phosphite and the mixture was stirred for 30 minutes at room temperature. The reaction mixture was then washed with water, dried over magnesium sulfate and filtered. The filtrate was evaporated to dryness and upon addition of a small quantity of acetone, a brown precipitate was formed. Upon addition of diethyl ether, the brown precipitate was decolored almost completely and after standing for one night in the refrigerator, the precipitate was filtered off to obtain 3.0 g (44.6%) of t-butyl 7-benzamido-3-bromomethyl-3-cephem-4-carboxylate 1-oxide.

NMR Spectrum (CDCl$_3$-DMSO-D$_6$): 1.57 (s, 9H), 3.44, 3.74, 3.79, 4.09 (ABq, 2H, J 18 Hz), 4.26, 4.42, 4.51, 4.67 (ABq, 2H, J 10.5 Hz), 4.90 (d, 1H, J 4.8 Hz), 6.20 (dd, 1H, J 4.8 and 9.5 Hz), 7.35–7.96 (m, 5H), 7.85 (d, 1H, J 9.5 Hz).

IR Spectrum: 3330, 1795, 1715, 1645, 1520, 1030 cm$^{-1}$.

The compound thus obtained was used as a reference in the following HPLC analysis. 248.1 mg of the product obtained in Example I(c) (with a purity of 78% according to quantitative NMR analysis) were dissolved in 10 ml of acetone and 0.05 ml of acetic acid were added to the solution. After cooling in an ice bath, 0.2 ml of trimethyl phosphite were added thereto and the mixture was held in the ice bath for another 10 minutes and then acetone was added until the volume of the mixture was exactly 25 ml. 5 ml of this solution were diluted once more with acetone to 25 ml and 5 ml of the thus obtained solution were used in the HPLC analysis. It was found that the solution contained 1.17 mg of t-butyl 7-benzamido-3-bromoethyl-3-cephem-4-carboxylate 1-oxide per ml from which it could be concluded that the yield of the debromination was 89%.

The remaining solutions were united and evaporated to dryness. After drying overnight in vacuo at room temperature, 242.2 mg of residue were obtained. If the debromination process had proceeded quantitatively, the residue would contain 66% of t-butyl 7-benzamido-3-bromomethyl-3-cephem-4-carboxylate 1-oxide and the quantitative NMR analysis indicated a 68% content. Thus, it can be concluded that the debromination process had indeed proceeded quantitatively.

EXAMPLE II

STEP A:

Portions of 1.71 g (9.6 mmoles) of N-bromosuccinimide were added over 1 hour to a solution of 2.02 g (5 mmoles) of t-butyl 7-phenylacetamido-3-methyl-3-cephem-4-carboxylate 1-oxide in 50 ml of dry methylene chloride under a nitrogen atmosphere and cooled in an ice bath while the mixture was irradiated with a 150 W tungsten lamp. The irradiation was continued for another 1.5 hours and then the solvent was removed by evaporation. The residue was dissolved in a small quantity of acetone whereupon the products were precipitated by adding petroleum ether (boiling point of 60° to 80° C.) to obtain 2.36 g of solid compounds.

STEP B:

625 mg of the solids thus obtained were dissolved in 40 ml of 1,2-dichloroethane and after filtering, the solution was diluted with acetone to 100 ml. 5 ml of this solution was diluted again with acetone to 25 ml. According to HPLC (High Performance Liquid Chromatography) analysis, the solution contained per ml: $1.0 \times 10^{-3}$ mmoles of t-butyl 3-bromomethyl-7-phenylacetamido-3-cephem-4-carboxylate 1-oxide, $0.17 \times 10^{-3}$ mmoles of t-butyl 2-bromo-3-methyl-7-phenylacetamido-3-cephem-4-carboxylate 1-oxide and $0.66 \times 10^{-3}$ mmoles of t-butyl 2-bromo-3-bromomethyl-7-phenylacetamido-3-cephem-4-carboxylate 1-oxide.

The starting material in the bromination process, i.e. t-butyl 7-phenylacetamido-3-methyl-3-cephem-4-carboxylate 1-oxide could not be detected anymore in the reaction mixture.

To other 5 ml portions of the original solution, a phosphite as specified below as each added at room temperature and these solutions were also each diluted with acetone to 25 ml. The results of the HPLC analysis of these solutions are summarized in the Table below.

| Phosphorus Compound | HPLC analysis ($10^{-3}$ mmoles/ml) | |
|---|---|---|
| | Starting Material | Desired Product |
| trimethyl phosphite | 0.18 | 1.7 |
| triisooctyl phosphite | 0.18 | 1.8 |
| triisodecyl phosphite | 0.18 | 1.7 |
| triphenyl phosphite | 0.17 | 1.8 |

It may be concluded that the 2-bromo compound and the 2-bromo-3-bromomethyl compound were completely converted by the phosphites into the corresponding debrominated products.

The reference 2-bromo-3-bromomethyl compound in the above HPLC analysis was prepared as follows: To a solution of 4.6 g (9.5 mmoles) of t-butyl 2-bromo-7-phenylacetamido-3-methyl-3-cephem-4-carboxylate 1-oxide in 350 ml of methylene chloride cooled in ice and irradiated with a 150 W tungsten lamp were added in portions over a period of 105 minutes 3.05 g (17.1 mmoles) of N-bromosuccinimide. After the addition was completed, the irradiation was continued for another hour and the orange-colored solution was concentrated to dryness by evaporation at low temperature. The residue was chromatographed on silica gel (elution with methylene chloride/acetone; first 72:1, then 49:1, v/v) to obtain 1.4 g (26%) of t-butyl 2-bromo-3-bromomethyl-7-phenylacetamido-3-cephem-4-carboxylate 1-oxide.

NMR Spectrum (CDCl$_3$): 1.55 (s, 9H), 3.58 (s, 2H), 4.16, 4.61 (ABq, 2H, J 11 Hz), 5.10 (d, 1H, J 5 Hz), 5.52 (s, 1H), 6.07 (dd, 1H, J 5 and 10 Hz), 6.76 (d, 1H, J 10 Hz), 7.26 (s, 5H).

IR Spectrum: 3350, 3260, 1790, 1705, 1670, 1500, 1060 cm$^{-1}$.

EXAMPLE III

STEP A:

A solution of 2-bromoethyl 7-phenylacetamido-3-methyl-3-cephem-4-carboxylate 1-oxide was brominated by the procedure of Step A of Example II. The reaction mixture obtained was subjected to a series of debromination reactions by the procedure of Step B of Example II with the phosphites listed below. The results of the HPLC analysis of the reaction mixtures resulting from the debromination processes, are summarized in the following Table. The first line in each Table relates to the HPLC analysis of the reaction mixture before the debromination reaction was carried out.

| Phosphorus compound | HPLC analysis ($10^{-3}$ mmoles/ml) | | |
|---|---|---|---|
| | I | II | III |
| Exp. 1 | | | |
| — | — | 2.3 | 0.08 |
| tributyl phosphite | 0.13 | 2.8 | — |
| triphenyl phosphite | 0.10 | 2.6 | — |
| diphenyl 2-ethylhexyl phosphite | 0.06 | 2.7 | — |
| diphenyl isooctyl phosphite | 0.07 | 2.6 | — |
| triisodecyl phosphite | 0.12 | 2.6 | — |
| Exp. 2 | | | |
| — | 0.32 | 2.6 | 0.28 |
| trimethyl phosphite | 0.46 | 2.7 | — |
| triethyl phosphite | 0.46 | 2.8 | — |
| triallyl phosphite | 0.44 | 2.8 | — |
| triisooctyl phosphite | 0.44 | 2.8 | — |

The reference compound II in this HPLC analysis, namely 2-bromoethyl 3-bromomethyl-7-phenylacetamido-3-cephem-4-carboxylate 1-oxide, was prepared as follows: To an ice-cooled solution of 2.28 g (5 mmoles) of 2-bromoethyl 7-phenylacetamido-3-methyl-3-cephem-4-carboxylate 1-oxide in 20 ml of 1,2-dichloroethane and 20 ml of acetic acid which was held under nitrogen and was irradiated with a 150 W tungsten lamp, 1.42 g (8 mmoles) of N-bromosuccinimide were added in portions over a period of 2 hours. The starting material had then disappeared completely and the solvent was removed by evaporation, 150 ml of ethyl acetate were added thereto and the resulting solution was washed sequentially with 2 portions of 250 ml of water, with a sodium bicarbonate solution and finally with water until neutral reaction. After drying over magnesium sulfate and filtering, the solution was evaporated until it was almost completely dry, and then 150 ml of diethyl ether were added thereto. The precipitate was collected by filtration to obtain 1.1 g (41% yield) of 2-bromoethyl 3-bromomethyl-7-phenylacetamido-3-cephem-4-carboxylate 1-oxide.

NMR Spectrum (DMSO-D$_6$): 3.40, 3.72, 3.88, 4.20 (ABq, 2H, J 19 Hz), 3.65 (s, 2H), 3.75 (t, 2H, J 6 Hz), 4.40, 4.56, 4.61, 4.77 (ABq, 2H, J 10 Hz), 4.64 (t, 2H, J 6 Hz), 4.99 (d, 1H, J 4.8 Hz), 5.89 (dd, 1H, J 4.8 and 8.8 Hz), 7.32 (s, 5H), 8.43 (d, 1H, J 8.8 Hz).

IR Spectrum: 3280, 1790, 1730, 1650, 1525, 1030 cm$^{-1}$.

The reference compound III in the HPLC analysis of the debromination mixture of the Example, 2-bromoethyl 2-bromo-7-phenylacetamido-3-methyl-3-cephem-4-carboxylate 1-oxide, was prepared by the procedure of Step B of Example I so that 2.58 g (5.7 mmoles) of 2-bromoethyl 7-phenylacetamido-3-methyl-3-cephem-4-carboxylate 1-oxide were converted into 2.50 g (82.5%) of the corresponding 2-bromo derivative.

NMR Spectrum (CDCl$_3$): 2.20 (s, 3H), 3.53 (t, 2H, J 6 Hz), 3.60 (s, 2H), 4.35, 4.55, 4.59 (t ABq, 2H, J 6 and 12 Hz), 5.11 (s, 1H), 5.12 (d, 1H, J 4.8 Hz), 6.11 (dd, 1H, J 4.8 and 9.5 Hz), 6.86 (d, 1H, J 9.5 Hz), 7.29 (s, 5H).

IR Spectrum: 3270, 1795, 1735, 1680, 1515, 1055 cm$^{-1}$.

The starting material, 2-bromoethyl 7-phenylacetamido-3-methyl-3-cephem-4-carboxylate 1-oxide, was prepared by the procedure of Step A of Example I and it was characterized as follows:

NMR Spectrum (DMSO-$D_6$): 2.05 (s, 3H), 3.38, 3.61, 3.64, 3.88 (ABq, 2H, J 14 Hz), 3.68 (s, 2H), 3.71 (t, 2H, J 5.5 Hz), 4.57 (t, 2H, J 5.5 Hz), 4.87 (d, 1H, J 4.5 Hz), 5.77 (dd, 1H, J 4.5 and 8.5 Hz), 7.30 (s, 5H), 8.32 (d, 1H, J 8.5 Hz).

IR Spectrum: 3280, 1770, 1730, 1655, 1530, 1035 $cm^{-1}$.

The reference compound IV was not available. Accordingly, although a quantitative increase of the concentration of compound II during the debromination process could be established, it was not possible to correlate this with a corresponding quantitative decrease of the concentration of compound IV.

EXAMPLE IV

A solution of t-butyl 7-formamido-3-methyl-3-cephem-4-carboxylate 1-oxide was brominated by the procedure of Step A of Example II and the experiment was repeated three times. The reaction mixture obtained was subjected to a series of debromination reactions by the procedure of Step B of Example II with the phosphites listed below. The results of the HPLC analysis of the reaction mixtures obtained before and after debromination, are summarized in the following Table.

| Phosphorus compound | HPLC analysis ($10^{-3}$ mmoles/ml) | | | |
|---|---|---|---|---|
| | I | II | III | IV |
| Exp. 1 | | | | |
| — | — | 1.0 | — | 0.97 |
| tributyl phosphite | — | 2.0 | — | — |
| Exp. 2 | | | | |
| — | — | 2.3 | — | 0.47 |
| tributyl phosphite | 0.05 | 2.6 | — | — |
| Exp. 3 | | | | |
| — | 0.11 | 3.7 | 0.81 | 1.1 |
| tributyl phosphite | 0.83 | 4.6 | — | — |
| Exp. 4 | | | | |
| — | 0.26 | 3.3 | 0.59 | 0.66 |
| tristearyl phosphite | 0.04 | 4.0 | — | — |
| distearyl pentaerythritol diphosphite | 0.79 | 4.0 | — | — |
| tris 25 phosphite | 0.77 | 3.8 | — | — |
| diphenyl didecyl (2,2,4-trimethyl-1,3-pentanediol) diphosphite | 0.73 | 4.1 | — | — |
| poly(dipropylemeglycol) phenyl phosphite | 0.96 | 3.7 | — | — |
| phenyl neopentylglycol phosphite | 0.78 | 3.7 | — | — |

The reference compound III in the HPLC analysis was prepared by the process of Step B of Example I and it was characterized as follows:

NMR Spectrum (CDCl$_3$): 1.57 (s, 9H), 2.22 (s, 3H), 5.18 (d, 1H, J 5 Hz), 5.22 (s, 1H), 6.15 (dd, 1H, J 5 and 10 Hz), 7.22 (d, 1H, J 10 Hz), 8.31 (s, 1H).

IR Spectrum: 3320, 1795, 1730, 1690, 1510, 1055 $cm^{-1}$.

The reference compound IV in the HPLC analysis was prepared as follows: To a solution of 4.71 g (15 mmoles) of t-butyl 7-formamido-3-methyl-3-cephem-4-carboxylate 1-oxide in 250 ml of methylene chloride, cooled in ice and irradiated with a 150 W tungsten lamp, 3.15 ml (22.5 mmoles) of triethylamine and 2.7 g (15 mmoles) of N-bromosuccinimide were added. After irradiation for 10 minutes, the starting material had disappeared completely according to TLC and the dark-brown solution thus obtained was washed twice with dilute hydrochloric acid solution (pH 1) and then twice with water. After drying over magnesium sulfate and filtering, the solution was concentrated by evaporation to approximately 100 ml. Then, 100 ml of acetic acid were added and the mixture was brominated as described hereinbefore with 2.7 g (15 mmoles) of N-bromosuccinimide. After irradiation for 1 hour, the conversion was not yet complete according to TLC. Again 1 g (5.6 mmoles) of N-bromosuccinimide was added and irradiation was continued for 30 minutes. Ethyl acetate was then added and methylene chloride was removed by evaporation in vacuo. Then, ice-water was added, the aqueous layer was separated and the remaining acetic acid was removed by washing with sodium bicarbonate solution. The organic layer was dried over magnesium sulfate, filtered and concentrated by evaporation in vacuo to approximately 100 ml. After removing some solid material by filtration, the residue was evaporated to dryness. The residue was treated with diethyl ether, petroleum ether was added and the product was filtered to obtain 4.58 g (64.7% yield) of t-butyl 2-bromo-3-bromomethyl-7-formamido-3-cephem-4-carboxylate 1-oxide (reference compound IV).

NMR Spectrum (CDCl$_3$-DMSO-$D_6$): 1.57 (s, 9H), 4.35, 4.38, 4.61, 4.65 (ABq, 2H, J 10.5 Hz), 5.35 (d, 1H, J 5 Hz), 5.90 (s, 1H), 6.14 (dd, 1H, J 5 and 9 Hz), 8.28 (s, 1H), 8.46 (d, 1H, J 9 Hz).

IR Spectrum: 3280, 1805, 1730, 1690, 1510, 1060 $cm^{-1}$.

EXAMPLE V

A solution of t-butyl 7-phenylacetamido-3-methyl-3-cephem-4-carboxylate 1-oxide was brominated by the procedure of Step A of Example II and the experiment was repeated twice more. The reaction mixture obtained was subjected to a series of debromination reactions by the procedure of Step B of Example II with the phosphorus compounds mentioned below. The results of the HPLC analysis of the mixtures obtained before and after debromination are summarized in the following Tables.

| Phosphorus Compond | | HPLC analysis ($10^{-3}$ mmoles/ml) | | | |
|---|---|---|---|---|---|
| | | I | II | III | IV |
| Exp. 1 | | | | | |
| — | | — | 0.60 | 0.06 | 0.31 |
| methyl diphenylphosphinite | | 0.05 | 0.93 | — | — |
| Exp. 2 | | | | | |
| — | | — | 3.1 | 0.28 | 0.69 |
| 2-ethoxy-4-methyl-1,3,2-dioxaphospholane | | 0.30 | 3.6 | — | — |
| 4-methyl-2-piperidino-1,3,2-dioxaphospholane | | 0.30 | 3.5 | — | — |
| | Phosphorus compound in mg/ml | | | | |
| Exp. 3 | | | | | |
| — | — | — | 2.2 | 0.19 | 0.45 |
| triallyl phosphite | 0.72 | 0.21 | 2.6 | — | — |
| triallyl phosphite | 1.6 | 0.21 | 2.6 | — | — |

The last experiment demonstrates that a large excess of debrominating agent may be used without affecting the net result.

EXAMPLE VI

A solution of 2,2,2-trichloroethyl 7-formamido-3-methyl-3-cephem-4-carboxylate 1-oxide was brominated by the procedure of Step A of Example II and the experiment was repeated three times. The reaction mixture obtained was subjected to a series of debromination reactions by the procedure of Step B of Example II with the phosphorus compounds mentioned below. The results of the HPLC analysis of the mixtures before and after debromination are summarized in the following Table.

| Phosphorus compound | HPLC analysis ($10^{-3}$ mmoles/ml) | | | |
|---|---|---|---|---|
| | I | II | III | IV |
| Exp. 1 | | | | |
| — | 0.07 | 1.9 | 0.24 | 0.49 |
| trimethyl phosphite | 0.31 | 2.3 | — | — |
| triisooctyl phosphite | 0.31 | 2.3 | — | — |
| triphenyl phosphite | 0.36 | 2.3 | — | — |
| diphenyl isodecyl phosphite | 0.31 | 2.3 | — | — |
| Exp. 2. | | | | |
| — | — | 1.5 | — | 1.1 |
| triallyl phosphite | — | 2.5 | — | — |
| tributyl phosphite | — | 2.5 | — | — |
| diphenyl 2-ethylhexyl phosphite | — | 2.5 | — | — |
| triisodecyl phosphite | — | 2.6 | — | — |
| methyl diphenylphosphinite | — | 2.5 | — | — |
| Exp. 3 | | | | |
| — | 0.10 | 1.4 | — | 0.36 |
| triethyl phosphite | 0.10 | 1.8 | — | — |
| diphenyl 2-ethylhexyl phosphite | 0.10 | 1.8 | — | — |
| diphenyl isooctyl phosphite | 0.10 | 1.8 | — | — |
| hexamethylphosphorous triamide | 0.10 | 1.6 | — | — |
| Exp. 4 | | | | |
| — | 0.05 | 2.6 | 0.6 | 0.82 |
| diethyl phenylphosphonite | 0.39 | 3.3 | — | — |
| 2-ethoxy-4-methyl-1,3,2-dioxaphospholane | 0.46 | 3.2 | — | — |
| diethyl N-methyl-N-phenylphosphoramidite | 0.46 | 3.3 | — | — |

The reference compound III in the HPLC analysis was prepared by the procedure of Step B of Example I and it was characterized as follows:

NMR Spectrum (CDCl$_3$): 2.34 (s, 3H), 4.96 (s, 2H), 5.25 (d, 1H, J 4.5 Hz), 5.29 (s, 1H), 6.22 (dd, 1H, J 4.5 and 10 Hz), 7.17 (s, 1H, J 10 Hz), 8.33 (s, 1H).

IR Spectrum: 3320, 1800, 1745, 1690, 1510, 1050 cm$^{-1}$.

The reference compound IV in the HPLC analysis was prepared by the procedure of Step B of Example IV and it was characterized as follows:

NMR Spectrum (CDCl$_3$): 4.21, 4.39, 4.68, 4.86 (ABq, 2H, J 11 Hz), 4.82 5.02, 5.03, 5.24 (ABq, 2H, J 12 Hz), 5.08 (d, 1H, J 5 Hz), 5.75 (s, 1H), 6.24 (dd, 1H, J 5 and 10 Hz), 7.57 (d, 1H, J 10 Hz), 8.32 (s, 1H).

IR Spectrum: 3270, 1810, 1750, 1690, 1505, 1055 cm$^{-1}$.

EXAMPLE VII

A solution of t-butyl 7-benzamido-3-methyl-3-cephem-4-carboxylate 1-oxide was brominated by the procedure of Step A of Example II and the experiment was repeated four times. The reaction mixture obtained was subjected to a series of debromination reactions by the procedure of Step B of Example II with the phosphorus compounds listed below. The result of the HPLC analysis of the reaction mixtures obtained before and after debromination are summarized in the following Table.

| Phosphorus compound | HPLC analysis ($10^{-3}$ mmoles/ml) | | | |
|---|---|---|---|---|
| | I | II | III | IV |
| Exp. 1 | | | | |
| — | — | 1.7 | 0.19 | 1.8 |
| 2-ethylhexyl dioctyl phosphite | 0.17 | 3.2 | — | — |
| tris-(2-chloroethyl)-phosphite | 0.17 | 3.2 | — | — |
| diphenyl isooctyl phosphite | 0.17 | 3.2 | — | — |
| Exp. 2 | | | | |
| — | — | 2.0 | 0.31 | 1.1 |
| triallyl phosphite | 0.31 | 3.1 | — | — |
| Exp. 3 | | | | |
| — | — | — | — | 1.8 |
| chlorodiphenylphosphine | — | 1.0 | — | 0.16 |
| Exp. 4 | | | | |
| — | — | 0.67 | 0.07 | 1.0 |
| benzyl diethyl phosphite | 0.07 | 1.7 | — | — |
| tri-o-tolyl phosphite | 0.06 | 1.5 | — | — |
| triauryl phosphite | 0.05 | 1.5 | — | — |
| diisodecyl pentaerythritol diphosphite | 0.06 | 1.6 | — | — |
| tetraphenyl dipropyleneglycol diphosphite | 0.06 | 1.6 | — | — |
| tris(dipropyleneglycol)phosphite | 0.09 | 1.6 | — | — |
| tetrakis(nonylphenyl)polypropyleneglycol diphosphite | 0.05 | 1.6 | — | — |
| Exp. 5 | | | | |
| — | — | 1.2 | 0.20 | |
| heptaki heptakis(dipropyleneglycol) triphosphite | 0.24 | 1.6 | — | — |
| tri(p-chlorophenyl)phosphite | 0.20 | 1.6 | — | — |

The preparation of the various reference compounds used in the HPLC analysis is described in Example I.

EXAMPLE VIII

A solution of methyl 7-phenylacetamido-3-methyl-3-cephem-4-carboxylate 1-oxide was brominated by the procedure of Step A of Example II. The reaction mixture was subjected to a series of debromination reactions by the procedure of Step B of Example II with the phosphites listed below. The results of the HPLC analysis of the reaction mixtures obtained before and after debromination are summarized in the following Table.

| Phosphorus Compound | HPLC analysis ($10^{-3}$ mmoles/ml) | | | |
|---|---|---|---|---|
| | I | II | III | IV |
| — | 0.08 | 1.2 | 0.20 | 0.23 |
| trimethyl phosphite | 0.28 | 1.4 | — | — |
| triallyl phosphite | 0.28 | 1.4 | — | — |
| diphenyl 2-ethylhexyl phosphite | 0.28 | 1.4 | — | — |

The reference compound III in the HPLC analysis was prepared by the procedure of Step B of Example I and it was characterized as follows:

NMR Spectrum (CDCl$_3$): 2.17 (s, 3H), 3.59 (s, 2H), 3.85 (s, 3H), 5.11 (d, 1H, J 4.8 Hz), 5.12 (s, 1H), 6.08 (dd, 1H, J 4.8 and 9.5 Hz), 6.92 (d, 1H, J 9.5 Hz), 7.30 (s, 5H).

IR Spectrum: 3300, 1795, 1735, 1680, 1515, 1055 cm$^{-1}$.

The reference compound IV in the HPLC analysis was prepared as follows: 1 g (1.8 mmol) of t-butyl 2-bromo-3-bromomethyl-7-phenylacetamido-3-cephem-4-carboxylate 1-oxide [prepared by the procedure of Step C of Example II] was dissolved in 15 ml of trifluoroacetic acid and after standing for 15 minutes at room temperature, the solution was evaporated to dryness. The residue was dissolved in methylene chloride and the solution was again evaporated to dryness. The residue was treated with diethyl ether and the product was isolated by filtration and was washed with diethyl ether and hexane to obtain 0.8 g (88% yield) of 2-bromo-3-bromomethyl-7-phenylacetamido-3-cephem-4-carboxylic acid 1-oxide.

NMR Spectrum ($CF_3COOD$): 3.98 (s, 2H), 4.12, 4.30, 4.81, 4.99, (ABq, 2H, J 11 Hz), 5.56 (d, 1H, J 5 Hz), 5.92 (s, 1H), 6.34 (d, 1H, J 5 Hz), 7.32 (s, 5H).

IR Spectrum: 3310, 2950, 1780, 1720, 1700, 1520, 1050 $cm^{-1}$.

To a solution of the product thus obtained in 20 ml of tetrahydrofuran, an excess of diazomethane in diethyl ether was added. When nitrogen generation was completed, the excess diazomethane was destroyed with acetic acid. The solution was then evaporated to dryness and the residue was dissolved in methylene chloride. The product precipitated upon addition of diethyl ether and hexane and was collected by filtration and was washed with hexane to obtain 0.63 g (77% yield) of methyl 2-bromo-3-bromomethyl-7-phenylacetamido-3-cephem-4-carboxylate 1-oxide (compound IV).

NMR Spectrum ($CDCl_3$): 3.60 (s, 2H), 3.89 (s, 3H), 4.15, 4.63 (ABq, 2H, J 10.5 Hz), 5.13 (d, 1H, J 5 Hz), 5.51 (s, 1H), 6.16 (dd, 1H, J5 and 10 Hz), 6.70 (d, 1H, J 10 Hz), 7.25 (s, 5H).

IR Spectrum: 3395, 1805, 1735, 1680 1510, 1045 $cm^{-1}$.

EXAMPLE IX

A solution of t-butyl 7-phenoxyacetamido-3-methyl-3-cephem-4-carboxylate 1-oxide was brominated by the procedure of Step A of Example II and the experiment was repeated. The reaction mixture was subjected to a series of debromination reactions by the procedure of Step B of Example II with the phosphites listed below. The results of the HPLC analysis of the reaction mixtures obtained before and after debromination are summarized in the following Table.

| Phosphorus Compound | HPLC analysis ($10^{-3}$ mmoles/ml) | | |
|---|---|---|---|
| | I | II | III |
| Exp. 1 | | | |
| — | — | 0.88 | 0.10 |
| triisooctyl phosphite | 0.10 | 1.4 | — |
| triisodecyl phosphite | 0.10 | 1.4 | — |
| tributyl phosphite | 0.10 | 1.4 | — |
| Exp. 2 | | | |
| — | — | 1.1 | 0.04 |
| diphenyl isodecyl phosphite | 0.04 | 1.4 | — |
| diphenyl isooctyl phosphite | 0.05 | 1.4 | — |
| triisodecyl phosphite | 0.05 | 1.4 | — |

The reference compound III in the HPLC analysis was prepared by the procedure of Step B of Example I and it was characterized as follows:

NMR Spectrum ($CDCl_3$): 1.56 (s, 9H), 2.19 (s, 3H), 4.57 (s, 2H), 5.14 (s, 1H), 5.16 (d, 1H, J 4.5 Hz), 6.16 (dd, 1H, J 4.5 and 10 Hz), approximately 6.78–7.50 (m, 5H), 7.82 (d, 1H, J 10 Hz).

IR Spectrum: 3370, 1800, 1730, 1700, 1520, 1055 $cm^{-1}$.

The comments with respect to reference compound IV at the end of Example III apply to the present reference compound IV as well.

EXAMPLE X

A solution of 2,2,2-trichloroethyl 7-phenoxyacetamido-3-methyl-3-cephem-4-carboxylate 1-oxide was brominated by the procedure of Step A of Example II and the experiment was repeated. The reaction mixture was subjected to a series of debromination reactions by the procedure of Step B of Example II with the phosphites listed below. The results of the HPLC analysis of the reaction mixtures obtained before and after debromination are summarized in the following Table.

| Phosphorus Compound | HPLC analysis ($10^{-3}$ mmoles/ml) | | |
|---|---|---|---|
| | I | II | III |
| Exp. 1 | | | |
| — | 0.15 | 0.79 | 0.39 |
| 2-ethylhexyl dioctyl phosphite | 0.57 | 1.0 | — |
| tris (2-chloroethyl) phosphite | 0.57 | 1.1 | — |
| diphenyl isodecyl phosphite | 0.55 | 1.0 | — |
| triethyl phosphite | 0.57 | 1.0 | — |
| Exp. 2 | | | |
| — | — | 1.0 | 0.10 |
| 2-ethylhexyl dioctyl phosphite | 0.12 | 1.3 | — |
| triisooctyl phosphite | 0.12 | 1.3 | — |
| tributyl phosphite | 0.12 | 1.3 | — |

The reference compound III in the HPLC analysis was prepared by the procedure of Step B of Example I and it was characterized as follows:

NMR Spectrum ($CDCl_3$): 2.30 (s, 3H), 4.56 (s, 2H), 4.94 (s, 2H), 5.18 (s, 1H), 5.22 (d, 1H, J 4.5 Hz), 6.23 (dd, 1H, J 4.5 and 10.5 Hz), approximately 6.77–7.50 (m, 5H), 7.81 (d, 1H, J 10.5 Hz).

IR Spectrum: 3320, 1800, 1745, 1695, 1520, 1055 $cm^{-1}$.

The comments in relation to reference compound IV at the end of Example III apply to the present reference compound IV as well.

EXAMPLE XI

A solution of benzhydryl 7-phenylacetamido-3-methyl-3-cephem-4-carboxylate 1-oxide was brominated by the procedure of Step A of Example II and the experiment was repeated twice more. The reaction mixture obtained was subjected to a series of debromination reactions by the procedure of Step B of Example II with the phosphorus compounds listed below. The results of the HPLC analysis of the reaction mixtures obtained before and after debromination are summarized in the following Table.

| Phosphorus compound | HPLC analysis ($10^{-3}$ mmoles/ml) | | |
|---|---|---|---|
| | I | II | III |
| Exp. 1 | | | |
| — | — | 1.2 | 0.03 |
| tributyl phosphite | 0.07 | 1.4 | — |

-continued

| Phosphorus compound | HPLC analysis (10⁻³ mmoles/ml) | | |
|---|---|---|---|
| | I | II | III |
| triallyl phosphite | 0.07 | 1.4 | — |
| 2-ethoxy-4-methyl-1,3,2-dioxaphospholane | 0.07 | 1.3 | — |
| Exp. 2 | | | |
| — | — | 1.2 | 0.17 |
| tributyl phosphite | 0.20 | 1.7 | — |
| triisodecyl phosphite | 0.20 | 1.8 | — |
| Exp. 3 | | | |
| — | 0.27 | 1.6 | 0.14 |
| triethyl phosphite | 0.47 | 1.8 | — |
| diphenyl 2-ethylhexyl phosphite | 0.45 | 1.8 | — |

Reference compound III in the HPLC analysis was prepared by the procedure of Step B of Example I and it was characterized as follows:

NMR Spectrum (CDCl₃): 2.14 (s, 3H), 3.63 (s, 2H), 5.14 (d, 1H, J 4.5 Hz), 5.17 (s, 1H), 6.08 (dd, 1H, J 4.5 and 10 Hz), 6.96 (s, 1H), approximately 7.15–7.63 (m, 16H).

IR Spectrum: 3360, 1790, 1735, 1685, 1520, 1050 cm⁻¹.

The comments in relation to reference compound IV at the end of Example III apply to the present reference compound IV as well.

EXAMPLE XII

A solution of benzyl 7-benzamido-3-methyl-3-cephem-4-carboxylate 1-oxide was brominated by the procedure of Step B of Example II. The reaction mixture obtained was subjected to debromination with the phosphites mentioned below. The results of the HPLC analysis obtained before and after the bromination has been carried out are summarized in the usual manner.

| Phoshphorus compound | HPLC analysis (10⁻³ mmoles/ml) | |
|---|---|---|
| | I | III |
| — | — | 2.0 |
| tributyl phosphite | 2.0 | — |
| triallyl phosphite | 2.0 | — |

The reference compound III in the HPLC analysis was prepared by the procedure of Step B of Example I and it was characterized as follows:

NMR Spectrum (CDCl₃): 2.23 (s, 3H), 5.19 (s, 1H), 5.24 (d, 1H, J 4.8 Hz), 5.31 (s, 2H), 6.32 (dd, 1H, J 4.8 and 10 Hz), approximately 7.22–8.12 (m, 11H).

IR Spectrum: 3400, 1795, 1730, 1670, 1520, 1050 cm⁻¹.

The starting material, benzyl 7-benzamido-3-methyl-3-cephem-4-carboxylate 1-oxide, was prepared by the procedure of Step A of Example I and it was characterized as follows:

NMR Spectrum (DMSO-D₆ in pyridine-D₅ 2:1): 2.12 (s, 3H), 3.93 (br., 2H), 5.27 (d, 1H, J 4.5 Hz), 5.44 (s, 2H), 6.36 (dd, 1H, J 4.5 and 9.5 Hz), 7.24–8.14 (m, 5H), 8.78 (d, 1H, J 9.5 Hz).

IR Spectrum: 3300, 1780, 1720, 1645, 1530, 1035 cm⁻¹.

EXAMPLE XIII

The procedure of Step A of Example XII was repeated using 4-nitrobenzyl 7-phenylacetamido-3-methyl-3-cephem-4-carboxylate 1-oxide as the starting material. The results of the following debromination procedure are summarized in the following Table.

| Phosphorus compound | HPLC analysis (10⁻³ mmoles/ml) | |
|---|---|---|
| | I | III |
| — | 0.04 | 2.2 |
| trimethyl phosphite | 2.5 | — |
| triethyl phosphite | 2.5 | — |
| triallyl phosphite | 2.5 | — |
| tributyl phosphite | 2.5 | — |

Reference compound III in the HPLC analysis was prepared by the procedure of Step B of Example I and it was characterized as follows:

NMR Spectrum (CDCl₃): 2.20 (s, 3H), 3.61 (s, 2H), 5.12 (s, 1H), 5.13 (d, 1H, J 4.5 Hz), 5.35 (s, 2H), 6.11 (dd, 1H, J 4.5 and 9.7 Hz), 6.85 (d, 1H, J 9.7 Hz), 7.31 (s, 5H), 7.50, 7.64, 8.15, 8.30 (ABq, 4H, J 9 Hz).

IR Spectrum: 3310, 1795, 1730, 1675, 1525, 1350, 1050 cm⁻¹.

The starting material, 4-nitrobenzyl 7-phenylacetamido-3-methyl-3-cephem-4-carboxylate 1-oxide, was prepared by the procedure of Step A of Example I and it was characterized as follows:

NMR Spectrum (CF₃CO₂D): 2.28 (s, 3H), 3.47, 3.81, 3.87 (s, 2H), 3.95, 4.28 (ABq, 2H, J 20 Hz), 5.03 (d, 1H, J 4 Hz), 5.55 (s, 2H), 6.23 (d, 1H, J 4 Hz), 7.34 (s, 5H), 7.60, 7.75, 8.23, 8.47 (ABq, 4H, J 8.5 Hz).

IR Spectrum: 3280, 1770, 1730, 1645, 1525, 1350, 1035 cm⁻¹.

EXAMPLE XIV

The procedure of Step A of Example XII was repeated using 4-methoxybenzyl 2-bromo-7-phenylacetamido-3-methyl-3-cephem-4-carboxylate 1-oxide as the starting material and the results of the following debromination procedure are summarized in the following Table.

| Phosphorus compound | HPLC analysis (10⁻³ mmoles/ml) | |
|---|---|---|
| | I | III |
| — | — | 1.9 |
| trimethyl phosphite | 2.0 | — |
| triethyl phosphite | 2.0 | — |
| triallyl phosphite | 2.0 | — |
| tributyl phosphite | 2.0 | — |

The reference compound III in the HPLC analysis was prepared by the procedure of Step B of Example I and it was characterized as follows:

NMR Spectrum (CDCl₃): 2.15 (s, 3H), 3.59 (s, 2H), 3.77 (s, 3H), 5.05 (d, 1H, J 4.8 Hz), 5.07 (s, 1H), 6.05 (dd, 1H, J 4.8 and 10 Hz), 6.81, 6.95, 7.26, 7.40 (ABq, 4H, J 9 Hz), 6.85 (d, 1H, J 10 Hz), 7.29 (s, 5H).

IR Spectrum: 3320, 1790, 1725, 1670, 1520, 1055 cm⁻¹.

EXAMPLE XV

A solution of t-butyl 2-bromo-3-bromomethyl-7-formamido-3-cephem-4-carboxylate 1-oxide was prepared by the procedure of Step D of Example IV and the results of the following debromination procedure are summarized in the following Table.

| Phosphorus compound | HPLC analysis (10⁻³ mmoles/ml) | |
|---|---|---|
| | II | IV |
| — | — | 5.1 |
| trimethyl phosphite | 4.7 | — |
| triethyl phosphite | 4.8 | — |
| tributyl phosphite | 4.8 | — |

EXAMPLE XVI

The procedure of Example XV was repeated using t-butyl 7-benzamido-3-methyl-3-cephem-4-carboxylate 1-oxide as a starting material. The results of the following debromination procedure are summarized in the following Table.

| Phosphorus compound | HPLC analysis (10⁻³ mmoles/ml) | |
|---|---|---|
| | II | IV |
| — | — | 2.8 |
| trimethyl phosphite | 2.6 | — |
| triethyl phosphite | 2.6 | — |
| tributyl phosphite | 2.6 | — |

The preparation of the reference compound IV has been described in Step C of Example I.

EXAMPLE XVII

To establish the influence of the solvent on the debromination process of the invention, a particular debromination reaction was studied using a variety of different solvents. In this procedure, a solid mixture of bromo derivatives of t-butyl 7-phenylacetamido-3-methyl-3-cephem-4-carboxylate 1-oxide was dissolved in acetic acid. To 2 ml of this solution, 20 ml of one of the solvents mentioned below and 0.1 ml of tributyl phosphite were added. Then, solvent was added until the total volume was 25 ml and the solutions thus prepared each contained 8% of acetic acid. The results of the HPLC analysis of the various experiments are listed below.

| Solvent | HPLC analysis (10⁻³ mmoles/ml) | | | |
|---|---|---|---|---|
| | I | II | III | IV |
| Exp. 1 | | | | |
| acetone (blank) | — | 1.6 | 0.12 | 0.23 |
| acetonitrile | 0.16 | 1.9 | — | — |
| acetic acid | 0.15 | 1.8 | — | — |
| N,N-dimethylacetamide | 0.15 | 1.8 | — | — |
| dioxane | 0.13 | 1.8 | — | — |
| acetone | 0.16 | 1.9 | — | — |
| 2-methoxyethanol | 0.18 | 1.7 | — | — |
| Exp. 2 | | | | |
| acetone (blank) | 0.03 | 2.4 | 0.57 | 0.39 |
| propylene carbonate | 0.64 | 2.7 | — | — |
| ethyl acetate | 0.62 | 2.8 | — | — |
| tetrahydrofuran | 0.62 | 2.8 | — | — |
| dimethoxyethane | 0.64 | 2.9 | — | — |

It may be concluded that the debromination process proceeds quantitatively in various types of solvents.

EXAMPLE XVIII

The procedure of Example XVII was repeated but t-butyl 7-benzamido-3-methyl-3-cephem-4-carboxylate 1-oxide was used as the starting material. The results of the HPLC analysis of the debromination process in still some other solvents are listed below.

| Solvents | HPLC analysis (10⁻³ mmoles/ml) | | | |
|---|---|---|---|---|
| | I | II | III | IV |
| acetone (blank) | — | — | 0.66 | 1.8 |
| bis(2-methoxyethyl) ether | 0.54 | 1.6 | — | — |
| tetrahydrothiophene 1,1-dioxide | 0.49 | 1.5 | — | — |

EXAMPLE XIX

To a solution of 10.1 g (25 mmoles) of t-butyl 7-phenylacetamido-3-methyl-3-cephem-4-carboxylate 1-oxide in 400 ml of dry methylene chloride which was held under nitrogen and cooled in an ice bath, 6.7 g (37.5 mmoles) of N-bromosuccinimide were added while the mixture was irradiated with a 150 W tungsten lamp. The irradiation was continued for 2.25 hours and then, the reaction mixture was washed with water and dried over magnesium sulfate. After evaporation to a small volume, the products were precipitated by addition of diethyl ether to obtain 7.6 g of a solid substance. 625 mg of the solid thus obtained were dissolved in 50 ml of acetone and 4 ml of this solution were diluted with acetone to 25 ml and subjected to HPLC analysis.

To other 4 ml samples of the solution, one of the debrominating agents mentioned below was added in approximately equimolar quantities. The sodium sulfite and sodium dithionite were dissolved in water, the stannous chloride in 4 N HCl solution. The results of the HPLC analysis before and after the debromination reaction are summarized in the following Table.

| Debromination agent | HPCL analysis (10⁻³ mmoles/ml) | | | |
|---|---|---|---|---|
| | I | II | III | IV |
| Exp. 1 | | | | |
| — | — | 2.6 | 0.21 | 0.56 |
| stannous chloride | — | 3.2 | — | — |
| Exp. 2 | | | | |
| — | — | 2.7 | 0.21 | 0.56 |
| sodium sulfite | 0.24 | 3.3 | — | — |
| Exp. 3 | | | | |
| — | — | 2.6 | 0.21 | 0.58 |
| sodium dithionite | 0.22 | 3.1 | — | — |

EXAMPLE XX

STEP A:

5.6 g of t-butyl 2-bromo-3-bromomethyl-7-phenylacetamido-3-cephem-4-carboxylate 1-oxide, prepared by the procedure of Step C of Example II, were dissolved in 40 ml of trifluoroacetic acid and the solution was stirred for 15 minutes at room temperature. The solvent was then evaporated, diethyl ether was added and the solvent was evaporated again. Diethyl ether was added again and the solid was filtered and dried under vacuum at room temperature to obtain 4.72 g (93.6% yield) of 2-bromo-3-bromomethyl-7-phenylacetamido-3-cephem-4-carboxylic acid 1-oxide as a pale yellow solid.

NMR Spectrum (DMSO-D6): 3.60 (s, 2H), 4.46 (s, 2H), 5.29 (d, 1H, J 4.5 Hz), 5.87 (dd, 1H, J 4.5 and 7.5 Hz), 6.09 (s, 1H), 7.20 (s, 5H), 8.53 (d, 1H, J 7.5 Hz).

IR Spectrum: 3340, 1790, 1730, 1705, 1620, 1525, 1040 cm⁻¹.

STEP B:

230.0 mg (0.45 mmoles) of the product of Step A were suspended in 2.5 ml of chloroform and then, 318 mg (1.32 mmoles) of trimethylsilyl trimethylsilylamidosulfonate were added and the mixture was stirred for 4 hours at 40° C. under nitrogen. According to the NMR spectrum, the solution contained trimethylsilyl 2-bromo-3-bromomethyl-7-phenylacetamido-3-cephem-4-carboxylate 1-oxide.

NMR Spectrum (CHCl$_3$): 0.33 (s, 9H), 3.65 (s, 2H), 4.23, 5.05 (ABq), 2H, J 10.5 Hz), 5.22 (d, 1H, J 5 Hz), 5.62 (s, 1H), 6.18 (dd, 1H, J 5 and 9.5 Hz), 6.96 (d, 1H, J 9.5 Hz), 7.3 (s).

STEP C:

55 mg of trimethyl phosphite were added to half of the solution of Step B. The NMR spectrum demonstrated clearly that debromination had taken place and that trimethylsilyl 3-bromomethyl-7-phenylacetamido-3-cephem-4-carboxylate 1-oxide was formed in situ.

NMR Spectrum (CHCl$_3$): 0.35 (s, 9H), approximately 3.2–4.2 (m), 4.30, 4.77 (ABq, 2H J 10.5 Hz), 4.63 (d, 1H, J 5Hz), 6.05 (dd, 1H, J 5 and 9.5 Hz), 7.05 (d, 1H, J 9.5 Hz), 7.4 (s).

EXAMPLE XXI

STEP A:

A quantity of approximately 0.2 mmoles of 2-bromo-3-bromomethyl-7-phenylacetamido-3-cephem-4-carboxylic acid 1-oxide was suspended in 10 ml of 1,2-dichloroethane and after the addition of about 0.7 mmoles of trimethylsilyl trimethylsilylamidosulfonate, the mixture was stirred for 1.5 hours at 30° C. under nitrogen. According to the NMR spectrum, the reaction mixture contained trimethylsilyl 2-bromo-3-bromomethyl-7-phenylacetamido-3-cephem-4-carboxylate 1-oxide.

STEP B:

The reaction mixture obtained in Step A was subjected to a series of debromination reactions with the phosphites mentioned below. Before the HPLC analysis was carried out, the trimethylsilyl 3-bromomethyl-7-phenylacetamido-3-cephem-4-carboxylate 1-oxide thus prepared was first converted into the corresponding methyl ester by adding each of the reaction mixtures obtained after the series of debromination reactions was carried out, to an excess of a solution of diazomethane in diethyl ether containing some methanol. When nitrogen was no longer evolved, the excess diazomethane was destroyed with acetic acid and the solvent was evaporated. The residue was dissolved in acetone and the volume of the solution was adjusted to 250 ml. This solution was then used in the HPLC analysis as described previously.

This procedure was repeated with another portion of the reaction mixture obtained in Step A to produce a solution of methyl 2-bromo-3-bromomethyl-7-phenylacetamido-3-cephem-4-carboxylate 1-oxide. The results of the HPLC analysis of these solutions of methyl esters, corresponding to the trimethylsilyl derivatives obtained before and after the debromination reactions were carried out, are summarized in the Table below.

| Phosphorus compound | HPLC analysis (10$^{-3}$ mmoles/ml) | |
|---|---|---|
|  | II | IV |
| Exp. 1 |  |  |
| — | — | 0.60 |
| tributyl phosphite | 0.58 | — |
| Exp. 2 |  |  |
| — | — | 0.56 |
| triisooctyl phosphite | 0.52 | — |
| Exp. 3 |  |  |
| — | — | 0.54 |
| triallyl phosphite | 0.62 | — |
| Exp. 4 |  |  |
| — | — | 0.46 |
| trimethyl phosphite | 0.47 | — |
| Exp. 5 |  |  |
| — | — | 0.56 |
| benzyl diethyl phosphite | 0.55 | — |
| Exp. 6 |  |  |
| — | — | 0.68 |
| bis-o-phenylene pyrophosphite | 0.60 | — |

EXAMPLE XXII

Trimethylsilyl 7-phenylacetamido-3-methyl-3-cephem-4-carboxylate 1-oxide was brominated by the process of Step A of Example II using 1,2-dichloroethane as a solvent. The reaction mixture was subjected to a debromination reaction by the procedure of Step B of Example II. The conversion of the products into corresponding methyl esters, before and after the debromination reaction was carried out, was effected as described in Example XXI.

The results of the HPLC analysis of the solutions of methyl esters thus obtained are summarized in the Table below.

| Phosphorus compound | HPLC analysis (10$^{-3}$ mmoles ml) | | | |
|---|---|---|---|---|
|  | I | II | III | IV |
| — | — | 0.23 | 0.04 | 0.07 |
| tributyl posphite | 0.03 | 0.30 | — | — |

Various modifications of the products and processes of the invention may be made without departing from the spirit or scope thereof and it is to be understood that the invention is intended to be limited only as defined in the appended claims.

We claim:

1. A process for the preparation of a compound of the formula

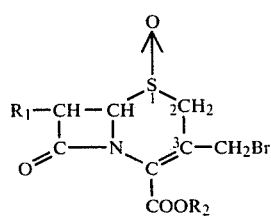

wherein $R_1$ is an acylamino and $R_2$ is a group protecting the carboxy radical comprising brominating a compound of the formula

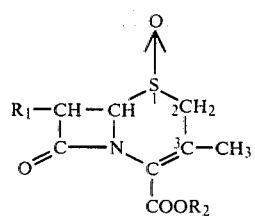

wherein $R_1$ and $R_2$ have the above definition to obtain a mixture of compounds of the formulae

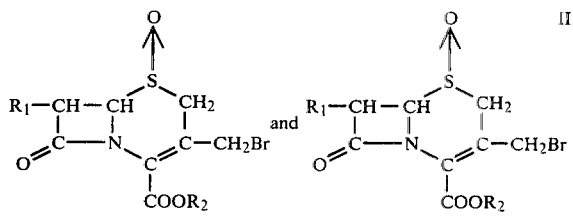

and treating the mixture or the compound of formula III with a debrominating agent selected from the group consisting of (a) phosphites of the formula

wherein $R_3$, $R_4$ and $R_5$ are individually selected from the group consisting of straight- or branched-chain alkyl optionally substituted with a chlorine atom and having 1 to 18 carbon atoms, phenyl optionally substituted with a methyl or chlorine, allyl and benzyl;

(b) phosphites selected from the group consisting of phenyl neopentylglycol phosphite, poly(dipropyleneglycol) phenyl phosphite, tris 25 phosphite and tris(dipropyleneglycol)phosphite;

(c) di- and triphosphites selected from the group consisting of diisodecyl pentaerythritol diphosphite, tetraphenyl dipropyleneglycol diphosphite, distearyl pentaerylthritol diphosphite, diphenyl didecyl (2,2,4-trimethyl-1,3-pentanediol) diphosphite, tetrakis(nonylphenyl)polypropyleneglycol diphosphite and heptakis(dipropyleneglycol) triphosphite;

(d) di(lower alkyl) phenylphosphonites;

(e) lower alkyl diphenylphosphinites;

(f) phosphines and (g) trivalent phosphorus compounds selected from the group consisting of hexamethylphosphorous triamide, 2-ethoxy-4-methyl-1,3,2-dioxaphospholane, 4-methyl-2-piperidino-1,3, 2-dioxaphospholane, diethyl N-methyl-N-phenylphosphoramidite and bis-o-phenylene pyrophosphite and an inorganic salt selected from the group consisting of stannous chloride, sodium sulfite and sodium dithionite in the presence of a hydrogen donor to selectively remove the 2-bromine.

2. The process of claim 1 wherein the debrominating agent is a trivalent organic phosphorus compound.

3. The process of claim 1 wherein the debrominating agent is an inorganic salt.

4. The process of claim 2 wherein the quantity of the debrominating agent is used in excess in relation to the quantity of the compound of formula III.

5. Process according to claim 3, wherein the debrominating agent is used in equimolar quantity in relation to the compound of formula III.

6. The process of claim 1 wherein the trivalent organic phosphorus compound is selected from the group consisting of trimethyl phosphite, triethyl phosphite, tripropyl phosphite, triisopropyl phosphite, tributyl phosphite, triisobutyl phosphite, triamyl phosphite, trioctyl phosphite, triisooctyl phosphite, tris (2-ethylhexyl) phosphite, tridecyl phosphite, triisodecyl phosphite, trineodecyl phosphite, trilauryl phosphite, tristearyl phosphite, triallyl phosphite, tris(2-chloroethyl) phosphite, triphenyl phosphite, tris(p-methylphenyl) phosphite, tris-o-tolyl phosphite, tris (p-chlorophenyl) phosphite, 2-ethylhexyl dioctyl phosphite, diethyl benzyl phosphite, didecyl phenyl phosphite, diisodecyl phenyl phosphite, isooctyl diphenyl phosphite, 2-ethylhexyl diphenyl phosphite, decyl diphenyl phosphite, isodecyl diphenyl phosphite, dimethyl phenylphosphonite, diethyl phenylphosphonite, di(t-butyl) phenylphosphonite, methyl diphenylphosphinite and ethyl diphenylphosphinite.

7. The process of claim 1 wherein the trivalent organic phosphorus compound is selected from the group consisting of trimethyl phosphite, triethyl phosphite, tributyl phosphite, triisooctyl phosphite, triisodecyl phosphite, trilauryl phosphite, tristearyl phosphite, triallyl phosphite, tris(2-chloroethyl) phosphite, triphenyl phosphite, tris-o-tolyl phosphite, tris(p-chlorophenyl) phosphite, 2-ethylhexyl dioctyl phosphite, diethyl benzyl phosphite, isooctyl diphenyl phosphite, 2-ethylhexyl diphenyl phosphite, isodecyl diphenyl phosphite, phenyl neopentylglycol phosphite, poly(dipropyleneglycol)phenyl phosphite, tris 25 phosphite, tris (dipropyleneglycol)phosphite, diisodecyl pentaerythritol diphosphite, tetraphenyl dipropyleneglycol diphosphite, distearyl pentaerythritol diphosphite, diphenyl didecyl (2,2,4-trimethyl-1,3-pentanediol) diphosphite, tetrakis(nonylphenyl) polypropyleneglycol diphosphite, heptakis (dipropyleneglycol) triphosphite, bis-o-phenylene pyrophosphite, hexamethylphosphorous triamide, 2-ethoxy-4-methyl-1,3,2-dioxaphospholane, 4-methyl-2-piperidino-1,3,2-dioxaphospholane, diethyl N-methyl-N-phenylphosphoramidite, diethyl phenylphosphonite, methyl diphenylphosphinite and chlorodiphenylphosphinte.

8. The process of claim 1 wherein the hydrogen donor is selected from the group consisting of water, a lower alkanol, for example, methanol and a carboxylic acid.

9. The process of claim 8 wherein the hydrogen donor is acetic acid.

10. The process of claim 1 wherein $R_1$ is selected from the group consisting of phenylacetamido, phenoxyacetamido, benzamido and formamido.

11. The process of claim 1 wherein $R_2$ is selected from the group consisting of a straight or branched-chain alkyl of 1 to 4 carbon atoms optionally substituted with at least one member of the group consisting of halogen and one to two phenyls, which phenyl groups may themselves carry at least one substituent selected from the group consisting of nitro and methoxy and $R_2$ is silyl group.

12. The process of claim 11 wherein $R_2$ is trilower alkylsilyl.

13. The process of claim 10 wherein $R_2$ is selected from the group consisting of methyl, t-butyl, 2-bromoethyl, 2,2,2-trichloroethyl, benzyl, 4-nitrobenzyl, 4-methoxybenzyl, benzhydryl and trimethylsilyl.

14. The process of claim 1 wherein the compound of formula III is separated from the reaction mixture, optionally purified and treated with a debrominating agent in the presence of a hydrogen donor.

15. A compound selected from the group consisting of t-butyl 7-benzamido-2-bromo-3-bromomethyl-3-cephem-4-carboxylate 1-oxide, 2,2,2-trichloroethyl 7-formamido-2-bromo-3-bromomethyl-3-cephem-4-carboxylate 1-oxide and methyl 2-bromo-3-bromomethyl-7-phenylacetamido-3-cephem-4-carboxylate 1-oxide.

* * * * *

UNITED STATES PATENT AND TRADEMARK OFFICE
CERTIFICATE OF CORRECTION

PATENT NO. : 4,182,870  Page 1 of 3
DATED : Jan. 8, 1980
INVENTOR(S) : CORNELIS A. BRUYNES and JAN J. de KONING It is certified that error appears in the above-identified patent and that said Letters Patent are hereby corrected as shown below:

Col. 2 Formula III   "$R_1\text{-CH-CH} \overset{O}{\underset{O}{\diagdown}} CH_2Br$" should be

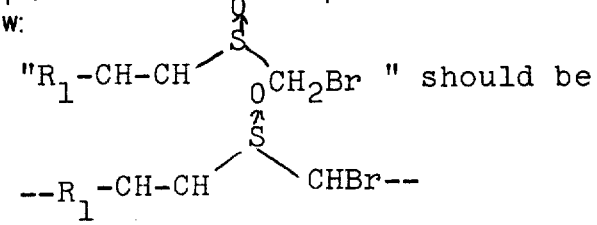

Col. 10 Line 10   " I II III" should be on the same line as Exp. 1

Col. 11 Line 31   "I II III IV " " " " " " " " " " " " "

Col. 12 Line 49   " " " " " " " " " " " " " " " " " "

Col. 13 Line 16   " " " " " " " " " " " " " " " " " "

Col. 14 Line 10   " " " " " " " " " " " " " " " " " "

Col. 14 Line 24   "triauryl" should be --trilauryl--

Col. 14 Line 32   Last Col. Left Out "0.46"

Col. 14 Line 33   First Col. Delete "heptaki

Col. 14 Line 54   "I II III IV" should be on the next line

Col. 15 Line 53   "I II III" should be on the same line as Exp. 1

Col. 16 Line 23   " " " " " " " " " " " " " " " " " "

Col. 16 Line 65   " " " " " " " " " " " " " " " " " "

UNITED STATES PATENT AND TRADEMARK OFFICE
CERTIFICATE OF CORRECTION

PATENT NO. : 4,182,870            Page 2 of 3
DATED : Jan. 8, 1980
INVENTOR(S) : CORNELIS A. BRUYNES and JAN J. de KONING It is certified that error appears in the above–identified patent and that said Letters Patent are hereby corrected as shown below:

Col. 16 Line 65    "I II III should be on the same line as Exp. 1"

Col. 17 Line 4    " " " " " " " " " " " " " " " " " " " "

Col. 17 Line 41    "I III should be on the next line

Col. 18 Line 7    " " " " " " " " " " " " " " " "

Col. 18 Line 45    " " " " " " " " " " " " " " " "

Col. 19 Line 4    "II IV " " " " " " " " " " " " "

Col. 19 Line 21    " " " " " " " " " " " " " " "

Col. 19 Line 48    "I II III IV should be on the same line as Exp 1

Col. 20 Line 11    " " " " " " should be on the next line

Col. 20 Line 38    " " " " " " should be on the same line as Exp. 1

Col. 21 Line 66    "II IV" should be on the same line as Exp. 1

Col. 22 Line 5    " " " " " " " " " " " " " " " " " " " "

UNITED STATES PATENT AND TRADEMARK OFFICE
CERTIFICATE OF CORRECTION

PATENT NO. : 4,182,870
DATED : Jan. 8, 1980
INVENTOR(S) : CORNELIS A. BRUYNES and JAN J. de KONING It is certified that error appears in the above-identified patent and that said Letters Patent are hereby corrected as shown below:

Col. 22 Line 42 "I II III IV" should be on the next line

Col. 23 Formula III  the portion of the formula reading

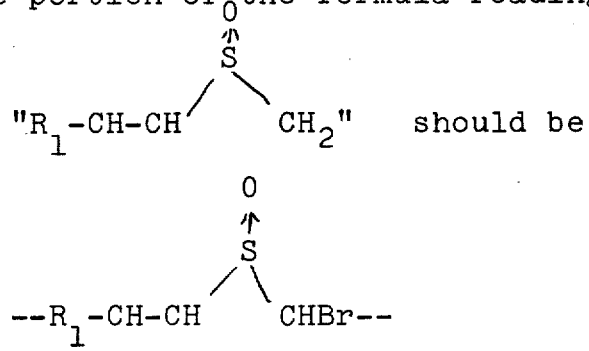

should be $$--R_1-CH-CH\underset{}{\overset{\overset{O}{\uparrow}{S}}{\diagup\diagdown}}CHBr--$$

Signed and Sealed this

*Seventeenth* Day of *June 1980*

[SEAL]

*Attest:*

SIDNEY A. DIAMOND

*Attesting Officer*    *Commissioner of Patents and Trademarks*